United States Patent [19]

Child et al.

[11] 4,187,373

[45] Feb. 5, 1980

[54] NOVEL DIHYDROBENZANTHRACENE DERIVATIVES

[75] Inventors: Ralph G. Child, Pearl River; Stanley A. Lang, Jr., Stony Point; Ving J. Lee, Airmont; Yang-i Lin, Nanuet, all of N.Y.

[73] Assignee: American Cyanamid Company, Stamford, Conn.

[21] Appl. No.: 947,976

[22] Filed: Oct. 2, 1978

[51] Int. Cl.$^2$ .................. C07D 233/56; C07D 239/20
[52] U.S. Cl. ................................. 542/402; 424/244; 424/251; 424/273 R
[58] Field of Search .......................................... 542/402

[56] References Cited
PUBLICATIONS

Pataki, et al; J. Med. Chem., 1971 (14) pp. 940–944.
Pataki, et al; J. Med. Chem., 1968 (11) pp. 1083–1086.

*Primary Examiner*—Arthur P. Demers
*Attorney, Agent, or Firm*—Edward A. Conroy, Jr.

[57] ABSTRACT

This disclosure describes benzanthracene-5,12(or 7,12)-dicarboxaldehyde-bis-hydrazones and the 5,12(or 7,12)-dihydrobenzanthracene-5,12(or 7,12)-dicarboxaldehyde-bis-hydrazones useful as antibacterial agents, for inhibiting the growth of transplanted mouse tumors, and for inducing the regression and/or pallation of leukemia and related cancers.

10 Claims, No Drawings

NOVEL DIHYDROBENZANTHRACENE DERIVATIVES

BRIEF SUMMARY OF THE INVENTION

This invention relates to new organic compounds and, more particularly, is concerned with novel benz[a]anthracene-7,12-bis-carbonyl-hydrazones (I), benz[b]anthracene-5,12-bis-carbonyl-hydrazones (II), 7,12-dihydrobenz[a]anthracene-7,12-bis-carbonyl-hydrazones (III), and 5,12-dihydrobenz[b]anthracene-5,12-bis-carbonyl-hydrazones (IV) which may be represented by the following structural formulae:

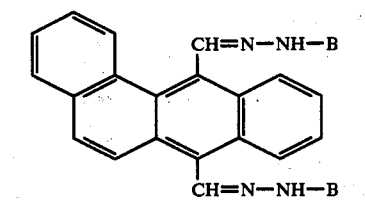

(I)

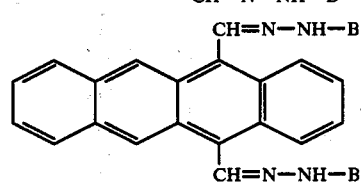

(II)

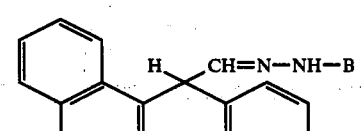

(III)

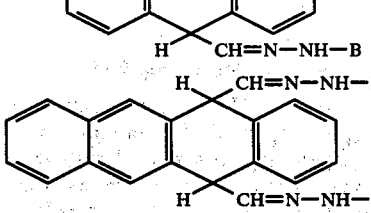

(IV)

wherein B is a monovalent moiety of the formula:

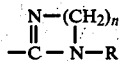

wherein n is 2, 3, 4 or 5 and R is hydrogen or alkyl having up to 4 carbon atoms.

The hydrazino substituents pendant from both the aromatic form and the dihydro form of the benzanthracene-5,12-(or 7,12)-bis-carbonyl nuclei may be the same or different and may be in the syn or anti forms. Additionally, in the case of the dihydro form, the entire units —CH=N—NH—B at the 5,12-positions or the 7,12-positions may be either cis (both extending out from the same face of the anthracene nucleus) or trans (extending out from the opposite faces of the anthracene nucleus).

A preferred embodiment of the present invention consists of compounds which may be represented by the following structural formulae:

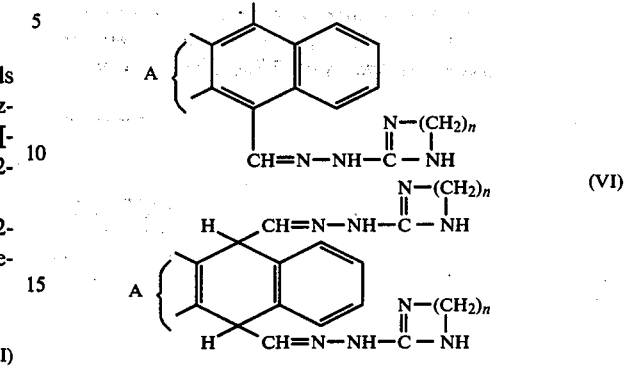

wherein A is a divalent moiety selected from the group consisting of those of the formulae:

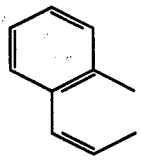 and 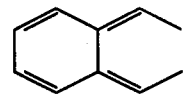

and n is as hereinabove defined.

DETAILED DESCRIPTION OF THE INVENTION

The novel compounds of the present invention are obtainable as yellow crystalline materials having characteristic melting points and absorption spectra and which may be purified by recrystallization from common organic solvents such as lower alkanols, dimethylformamide, tetrahydrofuran, methyl isobutyl ketone, and the like.

The organic bases of this invention form non-toxic acid-addition and quaternary ammonium salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. Quaternary ammonium salts may be formed by reaction of the free bases with one or more equivalents of a variety of organic esters of sulfuric, hydrohalic and aromatic sulfonic acids. The organic reagents employed for quaternary ammonium salt formation are preferably lower alkyl halides. However, other organic reagents are suitable for quaternary ammonium salt formation, and may be selected from among a diverse class of compounds including benzyl chloride, phenethyl chloride, naphthylmethyl chloride, dimethyl sulfate, methyl benzenesulfonate, ethyl toluenesulfonate, allyl chloride, methallyl bromide and crotyl bromide. For purposes of this invention the free bases are equivalent to their non-toxic acid-addition and quaternary ammonium salts. The acid-addition and quaternary ammonium salts of the organic bases of the present invention are, in general, crystalline solids, relatively soluble in water, methanol and ethanol but relatively insoluble in non-polar organic solvents such as diethyl ether, benzene, toluene, and the like.

The novel compounds of the present invention are useful as antimicrobial agents and possess antibacterial activity in vitro against a variety of standard laboratory microorganisms. The antibacterial spectrum in terms of the concentration required to inhibit the growth of various typical bacteria was determined in a standard manner by the agar-dilution streak-plate technique. A Steers multiple inocula replicator was used with incubation at 37° C. for 18 hours in Mueller-Ninton agar. The results for 7,12-bis-(2-imidazolin-2-ylhydrazone)benz-[a]anthracene-7,12-dicarboxaldehyde dihydrochloride, a typical compound of this invention, are set forth in Table I as the minimal inhibitory concentration (MIC) in micrograms per milliliter.

TABLE I

| Test Organism | MIC |
|---|---|
| *Staphylococcus aureus*, OSU 75-2 | 16 |
| *Staphylococcus aureus*, Q 74-11 | 8 |
| *Staphylococcus aureus*, St. Paul (NYC 78-1) | 8 |
| *Enterococcus*, SM 77-15 | 8 |

The novel compounds of the present invention also possess the property of inhibiting the growth of transplanted mouse tumors as established by the following tests.

Lymphocytic Leukemia P388Test

The animals used are mice all of one sex, weighing a minimum of 17 g. and all within a 3 gram weight range. There are 5 or 6 animals per test group. The tumor transplant is by intraperitoneal injection of 0.1 ml. or 0.5 ml. of dilute ascitic fluid containing $10^6$ cells of lymphocytic leukemia P388. The test compounds are administered intraperitoneally on days one, 5 and 9 (relative to tumor inoculation) at various doses. The animals are weighed and survivors are recorded on a regular basis for 30 days. The median survival time and the ratio of survival time for treated (T)/control (C) animals are calculated. The positive control compound is 5-fluorouracil given as a 60 mg./kg. injection. The results of this test with representative compounds of the present invention appear in Table II below. The criterion for efficacy is T/C×100≧125%.

TABLE II

| | Lymphocytic Leukemia P388 Test | | |
|---|---|---|---|
| Compound | Dose (mg./kg.) | Median Survival (Days) | T/C × 100 (Percent) |
| Bis(2-imidazolin-2-ylhydrazone) of 5,12-benz[b]-anthracenedicarboxaldehyde dihydrochloride | 12.5 | 22.0 | 191 |
| | 6.25 | 18.5 | 161 |
| | 3.12 | 18.0 | 157 |
| | 1.56 | 15.5 | 135 |
| | 0.78 | 15.0 | 130 |
| Control | 0 | 11.5 | — |
| 5-Fluorouracil | 60 | 12.5 | 109 |
| Bis(2-imidazolin-2-ylhydrazone) of 7,12-benz[a]-anthracenedicarboxaldehyde dihydrochloride | 12.5 | 19.0 | 190 |
| | 6.25 | 19.0 | 190 |
| | 3.12 | 17.5 | 175 |
| | 1.56 | 16.0 | 160 |
| | 0.78 | 15.0 | 150 |
| Control | 0 | 10.0 | — |
| 5-Fluorouracil | 60 | 20.0 | 200 |
| Bis(2-imidazolin-2-ylhydrazone) of 7,12-dihydro-benz[a]anthracene-7,12-dicarboxaldehyde | 25 | 20 | 182 |
| | 12.5 | 18 | 164 |
| | 6.25 | 16 | 145 |
| | 3.12 | 14 | 127 |
| | 1.56 | 14.5 | 132 |
| 5-Fluorouracil | 40 | 18 | 164 |
| Control | — | 11.0 | — |
| Bis(2-imidazolin-2-ylhydrazone) of 7,12-dihydro-benz[a]anthracene-7,12-dicarboxaldehyde dihydrochloride | 25 | 17 | 170 |
| | 12.5 | 17.5 | 175 |
| | 6.25 | 16.5 | 165 |
| | 3.12 | 16.5 | 165 |
| | 1.56 | 13.5 | 135 |
| | 0.78 | 13.0 | 130 |
| 5-Fluorouracil | 40 | 18.5 | 154 |
| Control | — | 10.0 | — |

Melanotic Melanoma B16

The animals used are C57BC/6 mice, all of the same sex, weighing a minimum of 17 g. and all within a 3 g. weight range. There are normally 10 animals per test group. A one-gram portion of melanotic melanoma B16 tumor is homogenized in 10 ml. of cold balanced salt solution and a 0.5 ml. aliquot of the homogenate is implanted intraperitoneally into each of the test mice. The test compounds are administered intraperitoneally on days one through 9 (relative to tumor inoculation) at various doses. The animals are weighed and survivors are recorded on a regular basis for 60 days. The median survival time and the ratio of survival time for treated (T)/control (C) animals are calculated. The positive control compound is 5-fluorouracil given as a 20 mg./kg. injection. The results of this test with a representative compound of the present invention appear in Table III below. The criterion for efficacy is T/C×100≧125%.

TABLE III

| | Melanotic Melanoma B16 | | |
|---|---|---|---|
| Compound | Dose (mg./kg.) | Median Survival (Days) | T/C × 100 (Percent) |
| Bis(2-imidazolin-2-ylhydrazone) of benz[a]anthra-cene-7,12-dicarboxaldehyde | 3 | 31.0 | 188 |
| | 1.5 | 30.5 | 185 |
| | 0.5 | 25.0 | 152 |
| | 0.2 | 22.0 | 133 |

TABLE III-continued

| | Melanotic Melanoma B16 | | |
|---|---|---|---|
| Compound | Dose (mg./kg.) | Median Survival (Days) | T/C × 100 (Percent) |
| Control | | 16.5 | |
| 5-Fluorouracil | 20 | 25.5 | 155 |

The novel compounds of formulae (I–IV) and their pharmacologically acceptable acid-addition and quaternary ammonium salts would be expected to show activity in standard test animals at doses substantially below toxic levels. The modes contemplated for administration are essentially parenteral and intraperitoneal. Solutions of the active ingredient as a free base or salt can be prepared in water or in water suitably mixed with, for example, surfactants such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical compositions can be in forms suitable for injectable use, which forms include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredient or ingredients in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the present compositions is contemplated. Supplementary active ingredients can also be incorporated into the inventive compositions.

It is especially advantageous to formulate compositions in dosage unit form for ease of administration and uniformity of dosage. Dosage unit form as used in the specification and claims herein refers to physically discrete units suited as unitary dosages for the animal subjects to be treated, each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as disclosed in detail in this specification.

The dosage of the principal active ingredient for the treatment of the indicated conditions depends upon the age, weight and condition of the subject being treated; the particular condition and its severity; the particular form of the active ingredient and the route of administration. A daily dose of from about one to about 100 mg./kg. of body weight given singly or in divided doses of up to 5 times a day embraces the effective range for the treatment of most conditions for which the novel compounds are effective and substantially non-toxic. For a 75-kg. subject, this translates into between about 75 and about 7500 mg./day. If the dosage is divided, for example, into 3 individual dosages, these will range from about 25 to about 2500 mg. of the active ingredient. The preferred range is from 2 to about 50 mg./kg. of body weight/day with about 2 to about 30 mg./kg./day being more preferred.

The principal active ingredient is compounded for convenient and effective administration in effective amounts with a suitable pharmaceutically-acceptable carrier in dosage unit form as hereinbelow disclosed. A unit dosage form can, for example, contain the principal active ingredient in amounts ranging from about 0.1 to about 400 mg., with from about one to about 30 mg. being preferred. Expressed in proportions, the active ingredient is generally present in from about 0.1 to about 400 mg./ml. of carrier. In the case of compositions containing supplementary active ingredients, the dosages are determined by reference to the usual dose and manner of administration of the said ingredients.

The aromatic benzanthracene derivatives of the present invention may be readily prepared as set forth in the following reaction scheme:

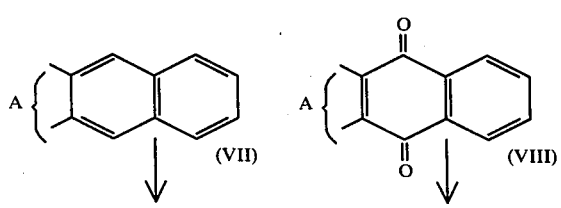

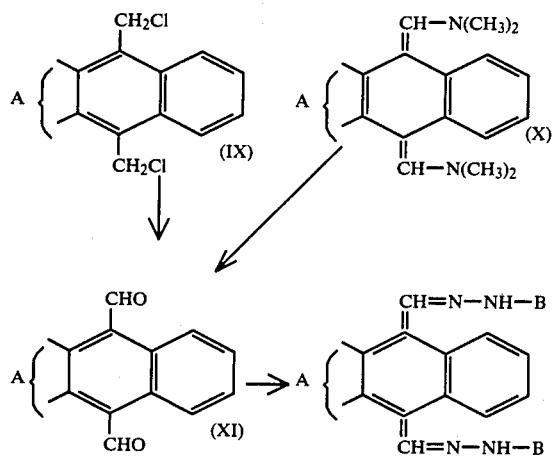

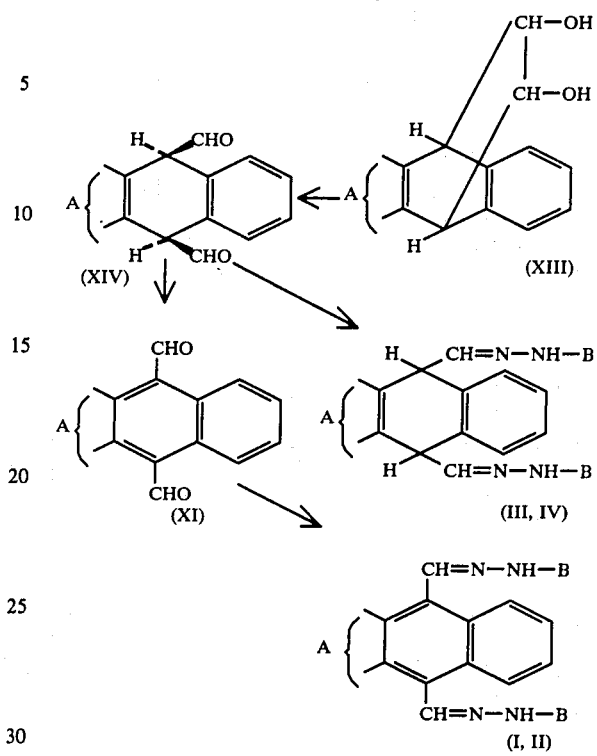

wherein A and B are as hereinbefore defined. In accordance with the above reaction scheme, the benzanthracene (VII) is treated with paraformaldehyde at the reflux temperature for 2-6 hours in a solution of dioxane and conc. hydrochloric acid which is saturated with gaseous HCl to provide the bis-(chloromethyl)benzanthracene (IX). This bis-(chloromethyl)benzanthracene, suspended in dry dimethyl sulfoxide under nitrogen at room temperature, is treated with sodium in ethanol to provide the intermediate benzanthracene-dicarboxaldehyde (XI). Alternatively, the benzanthraquinone (VIII) is dissolved in tetrahydrofuran and treated with an anhydrous diethyl ether-hexane solution of [α-lithio-α-(N,N-dimethylamino)methyl]diphenylphosphine oxide at room temperature to provide the bis-enamine (X) which, without isolation, is hydrolyzed by the addition of a 90% formic acid solution to give the intermediate benzanthracene-dicarboxaldehyde (XI). Treatment of (XI) with a hydrazine derivative of the formula H₂N—NH—B then provides the aromatic benzanthracene derivatives (I, II) of the present invention. This reaction is best carried out in a lower alkanol as solvent in the presence of an acid such as hydrochloric or acetic (or glacial acetic acid may be used as the sole solvent) usually at the reflux temperature of the reaction mixture.

The dihydrobenzanthracene derivatives of the present invention may be readily prepared as set forth in the following reaction scheme:

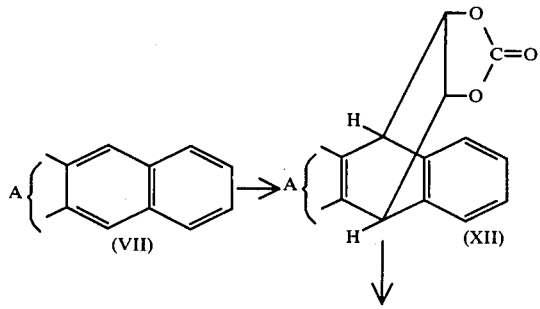

wherein A and B are as hereinbefore defined. In accordance with the above reaction scheme, the benzanthracene (VII) is heated with excess vinylene carbonate at reflux temperature under nitrogen for about 10-24 hours. Excess vinylene carbonate is removed by vacuum distillation. The residue is taken up in methylene chloride, clarified with charcoal, and precipitated with methanol to provide both the syn and anti forms of the cis-dihydro-ethanobenzanthracene cyclic carbonate (XII). Hydrolysis of the cyclic carbonate (XII) with aqueous-ethanolic potassium hydroxide at 70°-75° C. for about 1-4 hours produces both the syn and anti forms of the cis-dihydro-ethanobenzanthracene-diol (XIII) which in turn is treated with lead tetraacetate in glacial acetic acid at 20°-35° C. for about 10-30 minutes to give the dihydrobenzanthracene-dicarboxaldehyde (XIV). Alternatively, the diol (XIII) may be suspended in an aqueous solution of either sodium or potassium periodate and stirred at room temperature for 24 hours to provide the dicarboxaldehyde (XIV). Either procedure provides the cis-isomer of the dicarboxaldehyde (XIV) which may be readily converted to the trans form by standard procedures. Oxidation of the dihydrobenzanthracene-dicarboxaldehyde (XIV) with either ferric chloride in methanol or lead tetraacetate in glacial acetic acid, both at 20°-35° C. for 1-5 hours, then provides the benzanthracene-dicarboxaldehyde (XI). Treatment of XI and XIV with a hydrazine derivative of the formula H₂N—NH—B then provides the novel compounds (I, II, III and IV) of the present invention. This reaction is best carried out in ethanol or n-propanol at the reflux temperature for 1-4 hours in the presence of an acid such as hydrochloric acid or acetic acid.

The invention will be described in greater detail in conjunction with the following specific examples.

EXAMPLE 1

Bis(2-imidazolin-2-ylhydrazone)-7,12-dihydro-benz-[a]anthracene dicarboxaldehyde A 1.43 g. portion of 7,12-dihydro-benz[a]anthracene-7,12-dicarboxaldehyde [Neuman & Din, J. Org. Chem. 36, 966 (1971)] is dissolved in 100 ml. of boiling n-propanol. This solution is treated with 1.73 g. of 2-hydrazinoimidazoline dihydrochloride and the boiling is continued for 3 hours. The mixture is clarified by filtering while hot. The cooled filtrate produces an orange solid which is removed by filtration, washing with n-propanol. The combined filtrate and n-propanol washings is concentrated to ½ its volume, diluted to 200 ml. with water and basified with saturated aqueous sodium bicarbonate solution. The resulting gummy solid hardens and is then washed with water, collected by filtration, taken up in methanol and precipitated with water, giving the desired product as the base, m.p. 190°–195° C. This base is converted to its dihydrochloride salt by dissolving in n-propanol, treating with 6 N hydrochloric acid in n-propanol and cooling. The dihydrochloride salt melts at 245°–250° C.

EXAMPLE 2

5,12-Dihydro-5,12-benz[b]anthracene dicarboxaldehyde

A mixture of 7.0 g. of benz[b]anthracene and 26 g. of vinylene carbonate is heated at reflux under nitrogen for 20 hours. The excess vinylene carbonate is removed by vacuum distillation (57° C./9 mm.) and the residue is taken up in 25 ml. of methylene chloride and filtered. The filtrate is treated with twice its volume of methanol and then cooled, producing a tan solid and a mother liquor which is saved. This solid is recrystallized from 60 ml. of 1,2-dichloromethane, collected by filtration, washed with methanol and saved. The mother liquor (saved above) is concentrated giving a gummy solid which is recrystallized from a mixture of methylene chloride and methanol giving a gray solid which is combined with the above solid and recrystallized from ethyl acetate with charcoal treatment giving 5,12-dihydro-5,12-ethanobenz[b]anthracene-13,14-diol, cyclic carbonate as colorless rods. A mixture of 1.3 g. of the cyclic carbonate, 1.05 g. of potassium hydroxide, one ml. of water and 15 ml. of ethanol is stirred at 60°–65° C. for 2 hours. The mixture is diluted with 1-2 volumes of water, filtered and the solid is washed with water and dried giving cis-5,12-dihydro-5,12-ethanobenz[b]anthracene-13,14-diol as a colorless solid. To a solution of 2.6 g. of cis-5,12-dihydro-5,12-ethanobenz[b]anthracene-13,14-diol in 400 ml. of glacial acetic acid at 20° C. is added portionwise 4.4 g. of lead tetraacetate. The reaction is stirred for 45 minutes. The weakly purple colored solid is filtered off, washed with glacial acetic acid and finally water and dried leaving 1.0 g. (m.p. 170°–172° C.) of 5,12-dihydro-5,12-benz[b]anthracene dicarboxaldehyde.

EXAMPLE 3

Bis(2-imidazolin-2-ylhydrazone)-5,12-dihydro-5,12-benz[b]anthracene dicarboxaldehyde dihydrochloride A mixture of 0.85 g. of 5,12-dihydro-5,12-benz[b]anthracene dicarboxaldehyde and 1.04 g. of 2-hydrazinoimidazoline dihydrochloride in 60 ml. of n-propanol is boiled and concentrated to 30 ml. over the course of 2.5 hours. The solution is clarified by filtration and allowed to cool for 48 hours. The formed dark red crystals of the desired product weigh 0.12 g. and melt at 290°–295° C. More product may be obtained as the free base by diluting the mother liquor with water and basifying with sodium bicarbonate solution. The formed crude product is recrystallized from methanol giving 0.15 g. of dark red crystals melting at 230°–233° C.

EXAMPLE 4

7,12-Benz[a]anthracene dicarboxaldehyde

A mixture of isomers of 7,12-dihydro-7,12-benz[a]anthracene dicarboxaldehyde [Newman & Din, J. Org. Chem. 36, 967 (1971)] is suspended in 75 ml. of glacial acetic acid, treated with 6 g. of ferric chloride hexahydrate and stirred at room temperature for 3 hours. The remaining yellow solid is filtered off, washed with acetic acid and water leaving the yellow product, m.p. 197°–198° C.

EXAMPLE 5

Bis(2-imidazolin-2-ylhydrazone)-7,12-benz[a]anthracene dicarboxaldehyde dihydrochloride A solution of 0.57 g. of 7,12-benz[a]anthracene dicarboxaldehyde and 0.70 g. of 2-imidazolin-2-ylhydrazine in 50 ml. of n-propanol is boiled and concentrated to 20 ml. over the course of 3 hours. After cooling for 3 days, the formed orange powder is filtered off, washed with n-propanol and dried leaving the product, m.p. 240°–245° C. Dilution of the mother liquor with two volumes of water and basification with sodium bicarbonate solution gives the free base of the product as an orange solid, m.p. 210°–215° C.

EXAMPLE 6

5,12-Benz[b]anthracene dicarboxaldehyde

A solution of 5 g. of 13,14-dihydroxy-5,12-ethanobenz[b]anthracene in 110 ml. of glacial acetic acid is treated all at once with 15.4 g. of lead tetraacetate and stirred at 30°–40° C. for 3 hours. The formed purple solid is filtered, washed once with acetic acid, finally with water, dried and recrystallized from methylene chloride-methanol to give purple needles, m.p. 215°–217° C.

EXAMPLE 7

Bis(2-imidazolin-2-ylhydrazone)-5,12-benz[b]anthracene dicarboxaldehyde dihydrochloride A suspension of 1.0 g. of 5,12-benz[b]anthracene dicarboxaldehyde and 1.2 g. of 2-imidazolin-2-ylhydrazine in 75 ml. of n-propanol is boiled and concentrated to 50 ml. The formed solid material is filtered from the hot solution, washed with n-propanol, retaining the purple colored product, m.p. 320°–325° C.

We claim:

1. A compound selected from the group consisting of those of the formulae:

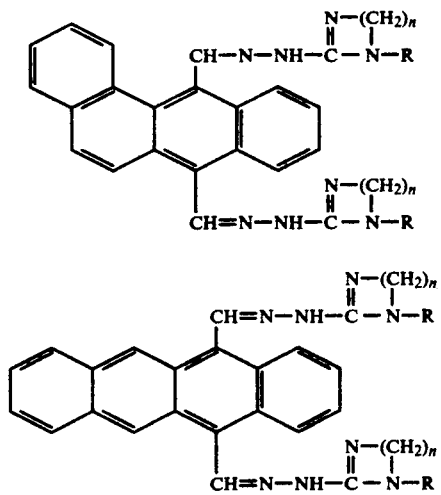

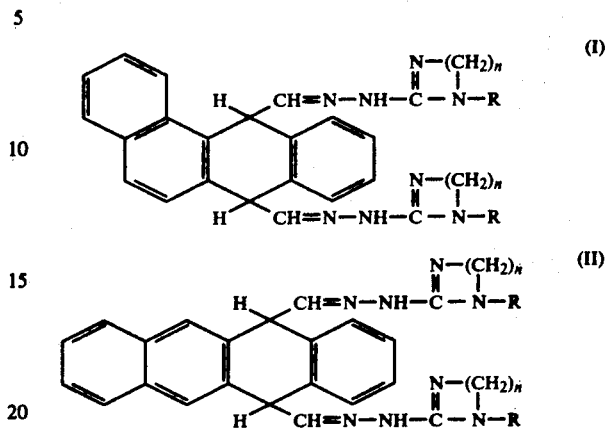

wherein n is 2, 3, 4 or 5 and R is hydrogen or alkyl having from 1 to 4 carbon atoms and the pharmaceutically acceptable acid-addition and quaternary ammonium salts thereof.

2. The compound according to claim 1, formula (I) thereof, wherein n is 2 and R is hydrogen; bis(2-imidazolin-2-ylhydrazone)-7,12-benz[a]anthracene dicarboxaldehyde.

3. The compound according to claim 1, formula (II) thereof, wherein n is 2 and R is hydrogen; bis(2-imidazolin-2-ylhydrazone)-5,12-benz[b]anthracene dicarboxaldehyde.

4. The compound according to claim 1, formula (I) thereof, wherein n is 4 and R is hydrogen; bis(4,5,6,7-tetrahydro-1H-1,3-diazepin-2-ylhydrazone)-7,12-benz[a]anthracene dicarboxaldehyde.

5. The compound according to claim 1, formula (II) thereof, wherein n is 3 and R is methyl; bis(1-methyl-1,3,4,5-tetrahydro-1H-pyrimid-2-ylhydrazone)-5,12-benz[b]anthracene dicarboxaldehyde.

6. A compound selected from the group consisting of those of the formulae:

wherein n is 2, 3, 4 or 5 and R is hydrogen or alkyl having from 1 to 4 carbon atoms and the pharmaceutically acceptable acid-addition and quaternary ammonium salts thereof.

7. The compound according to claim 6, formula (I) thereof, wherein n is 2 and R is hydrogen; 7,12-dihydro-bis(2-imidazolin-2-ylhydrazone)-7,12-benz[a]anthracene dicarboxaldehyde.

8. The compound according to claim 6, formula (II) thereof, wherein n is 2 and R is hydrogen; 5,12-dihydro-bis(2-imidazolin-2-ylhydrazone)-5,12-benz[b]anthracene dicarboxaldehyde.

9. The compound according to claim 6, formula (I) thereof, wherein n is 3 and R is hydrogen; 7,12-dihydro-bis(1,3,4,5-tetrahydro-1H-pyrimid-2ylhydrazone)-7,12-benz[a]anthracene dicarboxaldehyde.

10. The compound according to claim 6, formula (II) thereof, wherein n is 4 and R is methyl; 5,12-dihydro-bis(4,5,6,7-tetrahydro-1H-1,3-diazepin-2ylhydrazone)-5,12-benz[b]anthracene dicarboxaldehyde.

* * * * *